(12) United States Patent
Lee et al.

(10) Patent No.: US 11,577,221 B2
(45) Date of Patent: *Feb. 14, 2023

(54) SUPERABSORBENT POLYMER COMPOSITION

(71) Applicant: LG Chem, Ltd., Seoul (KR)

(72) Inventors: Jin Woo Lee, Daejeon (KR); Young Sam Kim, Daejeon (KR)

(73) Assignee: LG Chem, Ltd.

(*) Notice: Subject to any disclaimer, the term of this patent is extended or adjusted under 35 U.S.C. 154(b) by 790 days.

This patent is subject to a terminal disclaimer.

(21) Appl. No.: 16/477,783

(22) PCT Filed: Oct. 19, 2018

(86) PCT No.: PCT/KR2018/012434
§ 371 (c)(1),
(2) Date: Jul. 12, 2019

(87) PCT Pub. No.: WO2019/103317
PCT Pub. Date: May 31, 2019

(65) Prior Publication Data
US 2020/0122117 A1    Apr. 23, 2020

(30) Foreign Application Priority Data

Nov. 24, 2017  (KR) .................. 10-2017-0158933

(51) Int. Cl.
| | | |
|---|---|---|
| C08K 3/34 | (2006.01) | |
| C08K 5/092 | (2006.01) | |
| C08K 5/17 | (2006.01) | |
| A61L 15/60 | (2006.01) | |
| B01J 20/26 | (2006.01) | |
| B01J 20/28 | (2006.01) | |
| C08K 3/08 | (2006.01) | |
| C08L 33/06 | (2006.01) | |

(52) U.S. Cl.
CPC ............ *B01J 20/261* (2013.01); *A61L 15/60* (2013.01); *B01J 20/28016* (2013.01); *C08K 3/08* (2013.01); *C08K 3/34* (2013.01); *C08K 5/092* (2013.01); *C08K 5/175* (2013.01); *C08L 33/064* (2013.01); *B01J 2220/68* (2013.01); *C08K 2003/0856* (2013.01); *C08L 2203/02* (2013.01); *C08L 2312/00* (2013.01)

(58) Field of Classification Search
CPC ......... B01J 20/261; A61L 15/46; A61L 15/60; C08J 2300/14; C08K 5/092; C08K 5/0058; C08K 3/34; C08K 3/015
See application file for complete search history.

(56) References Cited

U.S. PATENT DOCUMENTS

| | | | |
|---|---|---|---|
| 6,469,080 B2 | 10/2002 | Miyake et al. | |
| 8,552,071 B1 | 10/2013 | Daniel et al. | |
| 8,846,823 B2 | 9/2014 | Nakamura et al. | |
| 2003/0135172 A1* | 7/2003 | Whitmore | A61L 15/60 |
| | | | 604/359 |
| 2007/0060691 A1 | 3/2007 | Kim | |
| 2008/0119626 A1 | 5/2008 | Fujimaru et al. | |
| 2008/0161512 A1 | 7/2008 | Kawano et al. | |
| 2010/0292078 A1 | 11/2010 | Braig et al. | |
| 2011/0068300 A1 | 3/2011 | Taniguchi et al. | |
| 2011/0245436 A1 | 10/2011 | Gartner et al. | |
| 2012/0202951 A1 | 8/2012 | Gartner et al. | |
| 2016/0074832 A1 | 3/2016 | Loick et al. | |
| 2017/0173207 A1* | 6/2017 | Hruza | A61L 15/46 |
| 2017/0216481 A1* | 8/2017 | Dhooge | A61L 15/20 |
| 2017/0216815 A1 | 8/2017 | Jang et al. | |
| 2018/0043332 A1 | 2/2018 | Lee et al. | |
| 2018/0228670 A1 | 8/2018 | Lee et al. | |
| 2021/0137754 A1* | 5/2021 | Sandin | A61L 15/34 |

FOREIGN PATENT DOCUMENTS

| | | | |
|---|---|---|---|
| CN | 1547488 A | | 11/2004 |
| EP | 2915547 A | * | 9/2015 |
| EP | 2915547 A1 | | 9/2015 |
| EP | 3056268 A1 | | 8/2016 |
| JP | H06016822 A | | 1/1994 |
| JP | H08067821 A | | 3/1996 |
| JP | H10298442 A | | 11/1998 |
| JP | H11116829 A | | 4/1999 |
| JP | 2001039802 A | | 2/2001 |
| JP | 2002530493 A | | 9/2002 |
| JP | 2004346089 A | | 12/2004 |
| JP | 2005304763 A | | 11/2005 |
| JP | 2012024537 A | | 2/2012 |
| JP | 2012526878 A | | 11/2012 |
| KR | 20070119040 A | | 12/2007 |
| KR | 20080069661 A | | 7/2008 |

(Continued)

OTHER PUBLICATIONS

The machine translation into English of KR-20190035313 A1; Lee et al; Year (2019).*
Extended European Search Report for Application No. 18880540.2 dated Feb. 20, 2020, 5 pages.
Third Party Observation for PCT/KR2018/012434 submitted Feb. 28, 2020, 18 pages.
International Search Report for Application No. PCT/KR2018/012434 dated Apr. 11, 2019, pp. 1-3.

*Primary Examiner* — Karuna P Reddy
(74) *Attorney, Agent, or Firm* — Lerner, David, Littenberg, Krumholz & Mentlik, LLP

(57) ABSTRACT

A superabsorbent polymer composition includes superabsorbent polymer particles, a chelating agent and a mixture of an organic acid and a silicate-based salt. The superabsorbent polymer particles include crosslinked polymer of water-soluble ethylenically unsaturated monomers including acid groups, of which at least a part are neutralized, and the chelating agent includes EDTA or an alkali metal salt thereof, exhibiting improved antimicrobial and deodorizing properties without deterioration of the superabsorbent polymer properties such as centrifugal retention capacity.

7 Claims, No Drawings

(56) References Cited

FOREIGN PATENT DOCUMENTS

| | | | |
|---|---|---|---|
| KR | 20120081113 | A | 7/2012 |
| KR | 20130086125 | A | 7/2013 |
| KR | 20160031983 | A | 3/2016 |
| KR | 20160068768 | A | 6/2016 |
| KR | 20170009546 | A | 1/2017 |
| KR | 20170068384 | A | 6/2017 |
| KR | 20170075624 | A | 7/2017 |
| KR | 101926161 | B1 | 12/2018 |
| KR | 20190035313 | A * | 4/2019 |
| WO | 9746190 | A1 | 12/1997 |
| WO | 9746191 | A1 | 12/1997 |
| WO | 9746194 | A1 | 12/1997 |
| WO | 9940953 | A1 | 8/1999 |
| WO | WO-0051651 | A1 * | 9/2000 |
| WO | 0071176 | A1 | 11/2000 |
| WO | 2014100777 | A2 | 6/2014 |
| WO | 2017099422 | A1 | 6/2017 |

* cited by examiner

SUPERABSORBENT POLYMER COMPOSITION

CROSS-REFERENCE TO RELATED APPLICATION(S)

The present application is a National Phase Entry under 35 U.S.C. § 371 of International Application No. PCT/KR2018/012434 filed Oct. 19, 2018, which claims priority from Korean Patent Application No. 10-2017-0158933 filed on Nov. 24, 2017 all of which are herein incorporated by reference.

TECHNICAL FIELD

The present invention relates to a superabsorbent polymer composition, more specifically to a superabsorbent polymer composition that may exhibit improved antimicrobial and deodorizing properties without deterioration of basic absorption performance.

BACKGROUND

Super absorbent polymer (SAP) is synthetic polymer material that can absorb moisture of 500 to 1000 times of self-weight, and is also named differently as super absorbency material (SAM), absorbent gel material (AGM), etc. according to developing companies. The superabsorbent polymer began to be commercialized as sanitary items, and currently, it is being widely used as hygienic goods such as a disposable diaper and the like, water-holding material for soil, water stop material for civil engineering and architecture, sheets for raising seedling, freshness preservatives in the field of food circulation, fomentation material, and the like, or in the field of electric insulation.

Such superabsorbent polymer is most widely applied for hygienic goods or disposable absorption products such as child diapers or adult diapers. Among them, in case applied for adult diapers, secondary odor resulting from bacterial growth significantly gives consumers an unpleasant feeling. In order to solve this problem, there have been attempts to introduce various deodorizing or antimicrobial functional components into a superabsorbent polymer composition before.

However, in the existing attempts to introduce various deodorizing/antimicrobial functional components, the antimicrobial/deodorizing properties of superabsorbent polymer were not sufficient, and there were disadvantages in that the stability of superabsorbent polymer may be deteriorated and the basic absorption performance may be deteriorated, or the unit cost of a superabsorbent polymer composition may be increased too much due to the high costs of functional components.

Therefore, there is a continued demand for the development of a superabsorbent polymer composition that exhibits more improved antimicrobial and deodorizing properties without deterioration of basic absorption performance, and has excellent economical efficiency.

Technical Problem

The present invention provides a superabsorbent polymer composition that exhibits improved antimicrobial and deodorizing properties without deterioration of basic absorption performance, and hygienic goods comprising the same.

Technical Solution

The present invention provides a superabsorbent polymer composition comprising:

superabsorbent polymer particles comprising crosslinked polymer of water-soluble ethylenically unsaturated monomers including acid groups, of which at least a part are neutralized;

a chelating agent including EDTA or an alkali metal salt thereof; and a mixture of organic acid and a silicate-based salt.

The present invention also provides hygienic goods comprising the superabsorbent polymer composition.

Effects of the Invention

According to the superabsorbent polymer composition, very improved antimicrobial property to bacteria inducing odor in hygienic goods such as an adult diaper, and the like, and the resulting deodorizing property can be exhibited without deterioration of basic absorption performance such as centrifugal retention capacity, absorbency under pressure, and the like. Particularly, such deodorizing/antimicrobial properties may be exhibited through the synergistic effect of raw materials having relatively low prices, thus contributing to the low unit cost and economic efficiency of the superabsorbent polymer composition.

DETAILED DESCRIPTION OF THE EMBODIMENTS

The terms used herein are only to explain specific embodiments, and are not intended to limit the present invention. A singular expression includes a plural expression thereof, unless it is expressly stated or obvious from the context that such is not intended. As used herein, the terms "comprise" or "include", etc. are intended to designate the existence of practiced characteristic, number, step, constructional element or combinations thereof, and they are not intended to preclude the possibility of existence or addition of one or more other characteristics, numbers, steps, constructional elements or combinations thereof.

Although various modifications can be made to the present invention and the present invention may have various forms, specific examples will be illustrated and explained in detail below. However, it should be understood that these are not intended to limit the present invention to specific disclosure, and that the present invention includes all the modifications, equivalents or replacements thereof without departing from the spirit and technical scope of the invention.

Hereinafter, a superabsorbent polymer composition according to specific embodiments of the present invention will be explained in more detail.

A superabsorbent polymer composition according to one embodiment of the invention comprises superabsorbent polymer particles comprising crosslinked polymer of water-soluble ethylenically unsaturated monomers including acid groups, of which at least a part are neutralized;

a chelating agent including EDTA or an alkali metal salt thereof; and a mixture of organic acid and a silicate-based salt.

According to the superabsorbent polymer composition of one embodiment, by using a chelating agent including EDTA or an alkali metal salt thereof having a relatively low unit cost, and a mixture of organic acid and a silicate-based salt, improved deodorizing/antimicrobial properties than previously known can be exhibited. Particularly, according to the result of continued experiments of the present inventors, due to the synergistic effect of the above explained two components, the growth of bacteria acting as an offensive odor component in an adult diaper, and the like may be very effectively inhibited, thereby effectively removing the offensive odor. As the result, it was confirmed that the superabsorbent polymer composition of one embodiment exhibits significantly improved deodorizing property.

And, these components do not inhibit the stability of the superabsorbent polymer composition, and thus, the superabsorbent polymer composition of one embodiment can maintain the basic absorption performance excellent, and the unit costs are relatively low, thus largely contributing to the low unit cost and economical efficiency of the superabsorbent polymer composition.

Therefore, the superabsorbent polymer composition of one embodiment can be very preferably applied for various hygienic goods such as an adult diaper, and the like.

Hereinafter, each component of the superabsorbent polymer composition of one embodiment will be explained in detail.

The superabsorbent polymer composition of one embodiment may comprise a chelating agent including EDTA or an alkali metal salt thereof; and a mixture of organic acid and a silicate-based salt, so as to achieve unique antimicrobial/deodorizing effects. And, as the chelating agent, those well known to a person having ordinary knowledge in the art, for example, a sodium salt of EDTA-2Na(EDTA-2Na) or amine acetic acid compounds may be used, and among them, a sodium salt of EDTA-2Na(EDTA-2Na) may be preferably used. In addition, amine acetic acid compounds selected from the group consisting of ethylene diamine tetraacetic acid, cyclohexane diamine tetraacetic acid, diethylene triamine pentaacetic acid, ethyleneglycol-bis-(aminoethylether)-N,N,N'-triacetic acid, N-(2-hydroxyethyl)-ethylene diamine-N,N,N'-triacetic acid, and triethylene tetraamine hexaacetic acid, or various chelating agents may be used.

Such a chelating agent may exist on the superabsorbent polymer particles to cause a synergistic effect with the mixture of organic acid and a silicate-based salt, and as the result, the superabsorbent polymer composition of one embodiment may exhibit improved deodorizing/antimicrobial properties.

More specifically, the chelating agent can act as an antimicrobial agent that inhibits the growth rate of various bacteria, particularly, the growth of odor-causing *Proteus mirabilis*. However, despite the growth inhibition action of the chelating agent, some bacteria may remain, thereby generating offensive odor due to the generation of ammonia, and the like. Such odor may be mostly removed by a mixture of organic acid and a silicate-based salt, and thus, the superabsorbent polymer composition of one embodiment may exhibit excellent deodorizing/antibacterial properties by the synergistic effect of two components.

The chelating agent may be included in the content of 0.1 to 5 parts by weight, or 0.5 to 3 parts by weight, or 0.9 to 2 parts by weight, based on 100 parts by weight of the superabsorbent polymer particles. By using the chelating agent, the growth rate of odor-causing *Proteus mirabilis* may be appropriately inhibited, and thus, excellent antimicrobial property may be exhibited, and a preferable range of antimicrobial property (CFU/ml) may be exhibited. Urea is converted into ammonia by *Proteus mirabilis*, and by inhibiting the growth of this bacterium, the amount of ammonia generated may be basically controlled low. Thus, the superabsorbent polymer composition of one embodiment may exhibit excellent antimicrobial/deodorizing properties. However, if the content of the chelating agent becomes too high, even bacteria beneficial to human body may be removed, or the stability or absorption property of superabsorbent polymer may be deteriorated.

Meanwhile, the superabsorbent polymer composition of one embodiment comprises a mixture of organic acid and a silicate-based salt. Such organic acid and silicate-based salt may also exist on the superabsorbent polymer particles.

Such a silicate-based salt may be in the form of a salt in which a silicate anion, and a cation of alkali metal or alkali earth metal are ionically bonded, and it may exist in the state of particles. Such silicate salt particles may include particles having a particle diameter of 150 μm or more and less than 600 μm in the content of about 80 to about 98 wt %, or about 90 to about 99 wt %, or about 92 to about 99.3 wt %.

And, the organic acid mixed with the silicate-based salt may exist on the superabsorbent polymer particles in the state of particles having a particle diameter of 600 μm or less, or 150 μm to 600 μm.

When the organic acid and silicate-based salt have the above-described particle properties and particle size distributions, they may be appropriately maintained on the superabsorbent polymer particles, and thus, can more selectively and effectively adsorb bacteria/offensive odor components to physically/chemically remove them. As the result, the superabsorbent polymer of one embodiment may exhibit more improved antimicrobial/deodorizing properties. Furthermore, due to the particle states, when mixed with superabsorbent polymer, anti-caking performance may be exhibited.

The organic acid may be included in the content of about 90 to 99.5 wt %, or about 95 to 99.3 wt %, or about 97 to 99.0 wt %, based on the total weight of the mixture of organic acid and a silicate-based salt. Thus, inside and/or on the surface of the superabsorbent polymer particles, a large number of acid sites may be generated. If such acid sites are included, various offensive odor components may be physically adsorbed, and the hydrogen cations(H+) of the acid sites may bond with offensive odor components to form ammonium salts, thereby more effectively removing offensive odor components.

The organic acid may include one or more selected from the group consisting of citric acid, fumaric acid, maleic acid and lactic acid, but it is not limited thereto.

Meanwhile, the mixture of organic acid and silicate-based salt may be mixed with superabsorbent polymer in which water-soluble ethylenically unsaturated monomers are polymerized, applied for hygienic goods such as a diaper, and the like.

According to one embodiment of the invention, the mixture of organic acid and a silicate-based salt may be included in the content of about 0.5 to about 5 parts by weight, or about 0.8 to about 5 parts by weight, or about 1 to about 4 parts by weight, based on 100 parts by weight of the superabsorbent polymer. If the contents of these components are too small, deodorizing property by the organic acid, and the like may not be sufficiently achieved, and if the contents are too large, the properties of superabsorbent polymer may be deteriorated.

The mixture of organic acid and a silicate-based salt may be prepared by a common method of mixing the organic acid and silicate-based salt. Although such a mixture may be prepared by previously mixing these two components, each component may be mixed with a chelating agent after preparing superabsorbent polymer particles, as described below.

Meanwhile, the kind or preparation method of the superabsorbent polymer that is mixed with the chelating agent, and the mixture of organic acid and a silicate-based salt may be those commonly used in the art, and the steps and method of mixing these components with the superabsorbent polymer are not specifically limited.

For example, the superabsorbent polymer may be obtained by progressing thermal polymerization or photopolymerization of a monomer composition comprising water soluble ethylenically unsaturated monomers and a polymerization initiator to obtain hydrogel polymer, and drying, grinding, sieving it, and if necessary, surface crosslinking or fine powder reassembly process, and the like may be further conducted.

For reference, throughout the specification, "superabsorbent polymer" means to include crosslinked polymer in which water-soluble ethylenically unsaturated monomers including acid groups, of which at least a part are neutralized, are polymerized; base polymer made in the form of powder by drying and grinding the crosslinked polymer; or those made suitable for the productization by subjecting the crosslinked polymer or base polymer to additional processes, for example, surface crosslinking, fine powder reassembly, drying, grinding, sieving, and the like, according to the context.

As the water-soluble ethylenically unsaturated monomers, any monomers commonly used for the preparation of superabsorbent polymer may be used without specific limitations. As the water-soluble ethylenically unsaturated monomers, one or more monomers selected from the group consisting of anionic monomers and salts thereof, non-ionic hydrophilic group containing monomers and amino group containing unsaturated monomers and quarternarized products thereof may be used.

Specifically, one or more selected from the group consisting of anionic monomers and salts thereof such as (meth)acrylic acid, maleic anhydride, fumaric acid, crotonic acid, itaconic acid, 2-acryloylethane sulfonic acid, 2-methacryloylethane sulfonic acid, 2-(meth)acryloyl propane sulfonic acid, or 2-(meth)acrylamido-2-methyl propane sulfonice acid; non-ionic hydrophilic group containing monomers such as (meth)acrylamide, N-substituted (meth) acrylate, 2-hydroxyethyl (meth)acrylate, 2-hydroxypropyl (meth)acrylate, methoxy polyethylene glycol (meth)acrylate, or polyethylene glycol (meth)acrylate; and amino group containing unsaturated monomers such as (N,N)-dimethylaminoethyl (meth)acrylate, (N,N)-dimethylaminopropyl (meth)acrylamide, and quarternarized products thereof, may be used.

More preferably, as the water soluble ethylenically unsaturated monomers, acrylic acid or salts thereof, for example, acrylic acid or an alkali metal salt such as a sodium salt thereof may be used, and in case such monomers are used, superabsorbent polymer having more excellent properties can be prepared. In case an alkali metal salt of acrylic acid is used as the water soluble ethylenically unsaturated monomers, acrylic acid may be neutralized with a basic compound such as caustic soda (NaOH) before use.

A polymerization initiator that is used when polymerizing the water-soluble ethylenically unsaturated monomers is not specifically limited as long as it is commonly used for the preparation of superabsorbent polymer.

Specifically, as the polymerization initiator, a thermal polymerization initiator or a photopolymerization initiator by UV irradiation may be used according to a polymerization method. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

According to one embodiment of the invention, the monomer composition may further comprise an internal crosslinking agent as the raw material of superabsorbent polymer. As the internal crosslinking agent, a crosslinking agent having one or more functional groups capable of reacting with the water soluble substituents of the water soluble ethylenically unsaturated monomers, and having one or more ethylenically unsaturated groups; or a crosslinking agent having two or more functional groups capable of reacting with the water soluble substituents of the monomers and/or the water soluble substituents formed by the hydrolysis of the monomers may be used.

As specific examples of the internal crosslinking agent, C8-12 bisacrylamide, bismethaacrylamide, C2-10 polyol poly(meth)acrylate or C2-10 polyol poly(meth)allylether, and the like may be mentioned, and more specifically, one or more selected from the group consisting of N,N'-methylene bis(methacrylate), ethylene oxy(methacrylate), polyethylene oxy(methacrylate), propylene oxy(methacrylate), glycerin diacrylate, glycerin triacrylate, trimethylol triacrylate, triallyl amine, triaryl cyanurate, triallyl isocyanate, polyethylene glycol, diethylene glycol and propylene glycol may be used.

In the preparation method, the monomer composition may further comprise additives such as a thickener, a plasticizer, a preservation stabilizer, an antioxidant, etc., as necessary.

The above explained raw materials such as water soluble ethylenically unsaturated monomers, a photopolymerization initiator, a thermal polymerization initiator, an internal crosslinking agent, and additives may be prepared in the form of a solution dissolved in a solvent.

Meanwhile, a method of forming hydrogel polymer by the thermal polymerization or photopolymerization of the monomer composition is not specifically limited in terms of its construction, as long as it is a commonly used polymerization method.

Specifically, the polymerization method is largely classified into thermal polymerization and photopolymerization according to an energy source. Commonly, thermal polymerization may be progressed in a reactor equipped with a stirring axis such as a kneader, and, photopolymerization may be progressed in a reactor equipped with a movable conveyer belt, but the above explained polymerization methods are no more than examples, and the present invention is not limited thereto.

Here, the moisture content of hydrogel polymer obtained by such a method may be about 40 to about 80 wt %. Throughout the specification, the "moisture content" is the content of moisture occupied based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is set up such that the temperature is raised from room temperature to about 180 L and then maintained at 180 L, and the total drying time is set up as 20 minutes including a temperature raising step of 5 minutes.

Next, the obtained hydrogel polymer is dried.

Wherein, a coarse grinding step may be further conducted before drying the hydrogel polymer so as to increase drying efficiency.

Here, grinders that can be used in the coarse grinding is not limited in terms of the constructions, but specifically, one selected from the group consisting of a vertical pulverizer, a turbo cutter, a turbo grinder, a rotary cutter mill, a cutter mill, a disc mill, a shred crusher, a crusher, a chopper, a disc cutter may be used, but the grinder is not limited thereto.

Through the coarse grinding step, the particle diameter of the hydrogel polymer may be controlled to about 2 to about 10 mm.

The hydrogel polymer coarsely ground as explained above, or hydrogel polymer immediately after polymerization that does not pass through the coarse grinding step is dried.

And, the drying method is not limited in terms of the construction as long as it is commonly used as a drying process of hydrogel polymer. Specifically, the drying step may be progressed by hot wind supply, infrared ray irradiation, ultrahigh frequency wave irradiation, or UV irradiation, etc. The polymer dried by such a method may exhibit a moisture content of about 0.1 to about 10 wt %. Next, the dried polymer obtained through the drying step is ground.

The particle diameter of the polymer powder obtained after the grinding step may be 150 μm to 850 μm. As a grinder for grinding to such a particle diameter, specifically, a pin mill, a hammer mill, a screw mill, a roll mill, a disc mill, or a jog mill, etc. may be used, but the grinder is not limited thereto.

And, in order to manage the properties of the superabsorbent polymer powders finally productized after the grinding step, the polymer powders obtained after grinding may be subjected to a separate process of sieving according to the particle diameter. Preferably, polymer having a particle diameter of about 150 to about 850 μm is sieved.

According to one embodiment of the invention, the ground or sieved polymer may be subjected to a step of surface crosslinking. Wherein, the surface crosslinking agent is not limited in terms of its construction as long as it can react with the functional group of the polymer. As examples of the surface crosslinking agent, polyhydric alcohol compounds, multivalent alkylene carbonate compounds, or multivalent epoxy compounds, and the like may be mentioned.

The superabsorbent polymer particles obtained by the above process, the above explained chelating agent, and the mixture of organic salt and a silicate-based salt may be uniformly mixed to obtain the superabsorbent polymer composition of one embodiment of the present invention.

Wherein, a method of mixing is not specifically limited, and for example, superabsorbent polymer particles, a chelating agent, organic acid and a silicate salt may be put into a reactor and mixed; or a solution comprising a chelating agent, organic acid and a silicate salt may be sprayed to superabsorbent polymer; or superabsorbent polymer, chelating agent, organic acid and silicate salt particles may be continuously fed into a reactor such as a continuously operated mixer and mixed; or organic acid and a silicate salt may be previously mixed, and then, superabsorbent polymer, a chelating agent, and the mixture of organic acid and a silicate salt may be continuously fed and mixed.

Meanwhile, in the superabsorbent polymer composition of one embodiment, the superabsorbent polymer particles may further comprise residual iron ions derived from a monomer composition comprising water soluble ethylenically unsaturated monomers and/or an initiator, in the content of 3 ppmw or less, or 0.1 to 3 ppmw, based on the total monomers.

In the preparation process of superabsorbent polymer particles, a polymerization initiator such as a common redox initiator, and the like may be used, and iron ions derived from the initiator may remain in the monomers and/or superabsorbent polymer particles. However, such iron ions may cause property deterioration of a superabsorbent polymer composition, but since the composition of one embodiment comprises a chelating agent, the residual amount of the iron ions may be reduced. As the result, the superabsorbent polymer composition of one embodiment may exhibit more excellent properties.

The superabsorbent polymer composition of one embodiment obtained as explained above may exhibit excellent antimicrobial/deodorizing effects and basic absorption properties.

Hereinafter, the actions and the effects of the invention will be explained in more detail, through specific examples of the invention. However, these examples are presented only as the illustrations of the invention, and the scope of the right of the invention is not limited thereby.

EXAMPLE

Example: Preparation of a Superabsorbent Polymer Composition

Example 1

100 parts by weight of acrylic acid monomers were mixed with 38.9 parts by weight of caustic soda(NaOH) and 103.9 parts by weight of water, and to the mixture, 0.1 parts by weight of a thermal polymerization initiator of sodium persulfate, 0.01 parts by weight of a photopolymerization initiator of diphenyl(2,4,6-trimethylbenzoyl)phosphine oxide, and 0.3 parts by weight of a crosslinking agent of polyethylene glycol diacrylate were added to prepare a monomer composition.

While the monomer composition was flowed at the flow rate of 243 kg/hr on the polymerization belt of a continuous belt polymerization reactor, of which internal temperature is maintained at 80 L, and on top of which a UV irradiation device having an intensity of 10 mW with a mercury UV lamp light source is installed, UV was irradiated for 1 minute, and a polymerization reaction was progressed for additional 2 minutes without a light source.

A gel type polymerization sheet emerging after the polymerization was finished was primarily cut using a Shredder type cutter, and then, coarsely ground through a meat chopper. Thereafter, it was dried at 180 L for 30 minutes through a hot air dryer, and then, ground using a rotary mixer and sieved to 180 μm to 850 μm, thus preparing base polymer.

Into the base polymer, 0.1 wt % of ethylene glycol diglycidyl epoxide were introduced and uniformly mixed, and then, a surface treatment was progressed at 140 L for 1 hour to obtain superabsorbent polymer.

Based on 100 parts by weight of the superabsorbent polymer, 1 part by weight of EDTA sodium salt (EDTA-2Na) and 1.01 parts by weight of a mixture including 99 wt % of citric acid and 1 wt % of sodium metasilicate salt were put in, and stirred at 500 rpm for 2 minutes using a Ploughshare blender. The prepared superabsorbent polymer composition was designated as Example 1.

Example 2

Superabsorbent polymer was prepared by the same method as Example 1.

Based on 100 parts by weight of the superabsorbent polymer, 1 part by weight of EDTA sodium salt (EDTA-2Na) and 2.02 parts by weight of a mixture including 99 wt % of citric acid and 1 wt % of sodium metasilicate salt were put in, and stirred at 500 rpm for 2 minutes using a Ploughshare blender. The prepared superabsorbent polymer composition was designated as Example 2.

Example 3

Superabsorbent polymer was prepared by the same method as Example 1.

Based on 100 parts by weight of the superabsorbent polymer, 1 part by weight of EDTA sodium salt (EDTA-2Na) and 3.03 parts by weight of a mixture including 99 wt % of citric acid and 1 wt % of sodium metasilicate salt were put in, and stirred at 500 rpm for 2 minutes using a Ploughshare blender. The prepared superabsorbent polymer composition was designated as Example 3.

Comparative Example 1

Superabsorbent polymer was prepared by the same method as Example 1. The prepared superabsorbent polymer itself was designated as Comparative Example 1.

Comparative Example 2

Superabsorbent polymer was prepared by the same method as Example 1.

Based on 100 parts by weight of the superabsorbent polymer, 1.01 parts by weight of a mixture including 99 wt % of citric acid and 1 wt % of sodium metasilicate salt were put in, and stirred at 500 rpm for 2 minutes using a Ploughshare blender. The prepared superabsorbent polymer composition was designated as Comparative Example 2.

Comparative Example 3

Superabsorbent polymer was prepared by the same method as Example 1.

Based on 100 parts by weight of the superabsorbent polymer, 2.02 parts by weight of a mixture including 99 wt % of citric acid and 1 wt % of sodium metasilicate salt were put in, and stirred at 500 rpm for 2 minutes using a Ploughshare blender. The prepared superabsorbent polymer composition was designated as Comparative Example 3.

Comparative Example 4

Superabsorbent polymer was prepared by the same method as Example 1.

Based on 100 parts by weight of the superabsorbent polymer, 3.03 parts by weight of a mixture including 99 wt % of citric acid and 1 wt % of sodium metasilicate salt were put in, and stirred at 500 rpm for 2 minutes using a Ploughshare blender. The prepared superabsorbent polymer composition was designated as Comparative Example 4.

Comparative Example 5

Superabsorbent polymer was prepared by the same method as Example 1.

Based on 100 parts by weight of the superabsorbent polymer, 1 part by weight of EDTA sodium salt (EDTA-2Na) was put in, and stirred at 500 rpm for 2 minutes using a Ploughshare blender. The prepared superabsorbent polymer composition was designated as Example 5.

Evaluation of the Properties of Superabsorbent Polymer

The properties of the superabsorbent polymer compositions of Examples 1 to 3 and Comparative Examples 1 to 5 were measured as follows, and the results were shown in Table 1.

(1) Antimicrobial/Deodorizing Performance Test 50 ml of artificial urine inoculated with 390,000 CFU/ml of *Proteus mirabillis* (ATCC 29906) was incubated in an oven of 35 L for 12 hours. The artificial urine and the artificial urine after incubated for 12 hours were designated as controls, properly washed with 150 ml of a saline solution to measure CFU (Colony Forming Unit), thereby calculating the properties of controls.

Each 2 g of the superabsorbent polymer compositions of Examples and Comparative Examples were added to 50 ml of the artificial urine inoculated with 390,000 CFU/ml of *Proteus mirabillis* (ATCC 29906), and then, incubated in an oven of 35 L for 12 hours. The artificial urine after incubated for 12 hours was properly washed with 150 ml of a saline solution to measure CFU (Colony Forming Unit). Thereby, the antimicrobial/deodorizing properties of each Example and Comparative Example were calculated/evaluated.

(5) CRC (Centrifugal Retention Capacity)

Centrifugal retention capacity (CRC) was measured according to EDANA method WSP 241.3. 0.2 g of the prepared superabsorbent polymer composition were put into a tea bag, and soaked in a 0.9% saline solution for 30 minutes. Thereafter, it was drained by gravity of 250 G for 3 minutes, and then, the amount of absorbed saline solution was measured.

TABLE 1

|  | Additives | Incubation time (hr) | CFU/ml | LOG [CFU/ml] | CRC (g/g) |
|---|---|---|---|---|---|
| Control | Superabsorbent polymer not added | 0 | 390000 | 5.6 |  |
|  |  | 12 | 110000000 | 8.04 |  |
| Example 1 | Superabsorbent polymer + Chelating agent (1 part by weight) + Citric acid + silicate salt (1.01 parts by weight) | 12 | 320000 | 5.5 | 35.4 |
| Example 2 | Superabsorbent polymer + Chelating agent (1 part by weight) + Citric acid + silicate salt (2.02 parts by weight) | 12 | 290000 | 5.5 | 34.7 |

TABLE 1-continued

| | Additives | Incubation time (hr) | CFU/ml | LOG [CFU/ml] | CRC (g/g) |
|---|---|---|---|---|---|
| Example 3 | Superabsorbent polymer + Chelating agent (1 part by weight) + Citric acid + silicate salt (3.03 parts by weight) | 12 | 170000 | 5.2 | 34.2 |
| Comparative Example 1 | Superabsorbent polymer | 12 | 3200000 | 6.5 | 37.4 |
| Comparative Example 2 | Superabsorbent polymer + Citric acid + silicate salt (1.01 parts by weight) | 12 | 740000 | 5.9 | 35.9 |
| Comparative Example 3 | Superabsorbent polymer + Citric acid + silicate salt (2.02 parts by weight) | 12 | 650000 | 5.8 | 35.0 |
| Comparative Example 4 | Superabsorbent polymer + Citric acid + silicate salt (3.03 parts by weight) | 12 | 350000 | 5.5 | 34.5 |
| Comparative Example 5 | Superabsorbent polymer + Chelating agent (1 part by weight) | 12 | 480000 | 5.8 | 35.9 |

Referring to Table 1, it was confirmed that the superabsorbent polymer compositions of Examples, despite the addition of the functional additives, maintain centrifugal retention capacities equivalent to or more excellent than those of Comparative Examples, and simultaneously, exhibit improved antimicrobial/deodorizing properties.

The invention claimed is:

1. A superabsorbent polymer composition comprising:
   superabsorbent polymer particles comprising a cross-linked polymer of water-soluble ethylenically unsaturated monomers including acid groups, wherein the acid groups are at least partially neutralized;
   a chelating agent including EDTA or an alkali metal salt thereof; and
   a mixture of an organic acid and a silicate-based salt,
   wherein the chelating agent is present in an amount of 0.1 to 5 parts by weight based on 100 parts by weight of the superabsorbent polymer particles, and
   wherein the organic acid is present in an amount of 90 wt % to 99 wt % based on a total weight of the mixture of the organic acid and the silicate-based salt, and
   wherein the mixture of the organic acid and the silicate-based salt is present in an amount of 0.5 to 5 parts by weight based on 100 parts by weight of the superabsorbent polymer particles wherein the organic acid comprises citric acid, fumaric acid, maleic acid or lactic acid, and
   wherein the silicate-based salt includes a salt in which a silicate anion, and a cation of alkali metal or alkaline metal are bonded.

2. The superabsorbent polymer composition according to claim 1, wherein the chelating agent comprises a sodium salt of EDTA (EDTA-2Na).

3. The superabsorbent polymer composition according to claim 1, wherein the superabsorbent polymer particles further comprise residual iron ions derived from a monomer composition comprising water soluble ethylenically unsaturated monomers and an initiator in a content of 3 ppmw or less.

4. A hygienic good comprising the superabsorbent polymer composition of claim 1.

5. The superabsorbent polymer composition according to claim 1, wherein the chelating agent further comprises an amine acetic acid compound, wherein the amine acetic acid comprises ethylene diamine tetraacetic acid, cyclohexane diamine tetraacetic acid, diethylene triamine pentaacetic acid, ehtyleneglycol-bis-(aminoethylether)-N,N,N'-triacetic acid, N-(2-hydroxyethyl)-ethylene diamine-N,N,N'-triacetic acid, or triethylene tetraamine hexaacetic acid.

6. The superabsorbent polymer composition according to claim 3, wherein the residual iron ions are in the content of 0.1 to 3 ppmw.

7. The superabsorbent polymer composition according to claim 1, wherein the silicate-based salt is sodium metasilicate salt.

* * * * *